United States Patent [19]

della Faille d'huysse et al.

[11] 4,259,640
[45] Mar. 31, 1981

[54] PROCESS AND DEVICE FOR DETERMINING A CHEMICAL DEICER ON A ROAD

[75] Inventors: Gaëtan della Faille d'huysse, Brussels; Jacques Clausse, Waterloo; Louis Boxus, Sint-Stevens-Woluwe, all of Belgium

[73] Assignee: Solvay & Cie., Brussels, Belgium

[21] Appl. No.: 49,157

[22] Filed: Jun. 18, 1979

[30] Foreign Application Priority Data

Jun. 21, 1978 [FR] France .................. 78 18780
Jan. 12, 1979 [FR] France .................. 79 00921

[51] Int. Cl.³ .................................. G01N 27/42
[52] U.S. Cl. .................................. 324/439; 324/65 R
[58] Field of Search ................ 324/439, 425, 65 R

[56] References Cited

U.S. PATENT DOCUMENTS

| 3,293,155 | 12/1966 | Stone ........................ 324/439 |
| 3,484,805 | 12/1969 | Lorenz ...................... 324/439 |
| 3,542,113 | 11/1970 | Mostofin .................... 324/439 |
| 3,914,688 | 10/1975 | Lev .......................... 324/439 |

FOREIGN PATENT DOCUMENTS 2061899 10/1969 France .

OTHER PUBLICATIONS

H₂O Tijdschrift Voor Waternootziening en Afvalwater Behandeling, vol. 10, Nov. 24, 1977, p. N96.

Primary Examiner—Michael J. Tokar
Attorney, Agent, or Firm—Spencer & Kaye

[57] ABSTRACT

A process for determining a chemical deicer on a road comprising positioning a shell on the road, introducing a fixed amount of solvent for the deicer into the shell to form a layer of solution, and measuring an electrical parameter of the resulting layer of solution. A device for carrying out this process is also disclosed.

10 Claims, 5 Drawing Figures

PROCESS AND DEVICE FOR DETERMINING A CHEMICAL DEICER ON A ROAD

BACKGROUND OF THE INVENTION

The aim of the present invention is to provide a process for checking the condition of the roads in winter and more particularly during periods of frost or snowfall.

It relates more particularly to a process for determining the amount of chemical deicer present on a road.

In order to ensure that the roads are in good condition during periods of frost or snowfall, and in particular to preserve an adequate grip thereon, it is common practice to spread chemical deicers, such as, for example, an alkali metal chloride or alkaline earth metal chloride, urea, alcohols and the like, on the roads.

Although these chemical deicers can be spread on the roads after a slippery layer of frost, ice or snow has formed thereon, in order to melt the layer, they generally prove more active, however, when they are spread as a preventive measure, that is to say before a slippery layer of this kind has had the time to form. This practice exhibits the additional advantage that it permanently prevents the formation of a layer of ice, frost or snow on the roads, which is obviously likely to increase the safety of the users.

However, the spreading of chemical deicers as a preventive measure exhibits the disadvantage that they are gradually removed from the roads by the effect of traffic and wind, and also by run-off during precipitation, with the result that it proves necessary to carry out periodic spreading operations. It is therefore important to be able periodically to check whether the amount of chemical deicer present per unit area of the road is adequate for the safety of the users. For this purpose, it has already been proposed to measure the electrical resistance of the film of chemical deicer which covers the road ($H_2O$-Tijdschrift voor watervoorziening en afvalwaterdeling, Volume 10, Nov. 24th, 1977, page N96; French Pat. No. 2,061,899). Although it is easy and rapid, this known checking process has proved unreliable in practice because it is incapable of ensuring a precise and reproducible measurement of the amount of deicer present on the road.

SUMMARY OF THE INVENTION

The present invention overcomes this disadvantage of this known process by providing a process which makes it possible to check, easily, rapidly and precisely, the amount of chemical deicer present on a road.

For this purpose, the invention relates to a process for determining a chemical deicer on road, in accordance with which process a shell of predetermined cross-section is placed on the road, a fixed amount of a solvent for the chemical deicer is introduced into the compartment delimited by the shell and the road, and an electrical parameter of the resulting layer of solution is measured.

BRIEF DESCRIPTION OF THE DRAWINGS

In these Figures, identical elements are denoted by the same reference numbers.

DETAILED DESCRIPTION OF THE INVENTION

In the process according to the invention, the term chemical deicer is understood as meaning a substance which is capable of lowering the freezing point of water sufficiently to prevent the formation of layers of ice, frost or snow in a normal winter. Chemical deicers which are commonly used on roads, within the scope of the invention, are alkali metal or alkaline earth metal chlorides in the particulate state or in aqueous solutions, for example sodium chloride and calcium chloride. Mixtures of sodium chloride and calcium chloride are advantageously used.

The shell serves the purpose of delimiting a surface of defined area on the road. The shape of its cross-section is not critical; for example, it can be circular, oval or polygonal. The shell must nevertheless be designed so as to ensure a leaktight contact with the road. For this purpose, it can be equipped with, for example, a leaktight elastic strip on its edge which is intended to be applied to the surface of the road.

In the process according to the invention, a solvent which does not react with the material constituting the road, for example with the hydrocarbon surfacings, is preferably chosen. Solvents of low volatility, in which the chemical deicer dissolves rapidly, are preferably used. Aqueous solvents, in particular water, constitute a class of solvents which are preferred within the scope of the invention. In times of intense cold, it can prove necessary to employ a solvent of low melting point, for example a mixture of water and acetone. In this particular case, the proportion of acetone in the water/acetone mixture depends on the temperature; in general, it can advantageously be fixed at between 5 and 25% of the weight of the mixture. In order to accelerate the dissolution of the chemical deicer in the solvent, the latter cann optionally be heated before it is introduced into the shell.

According to the invention, the amount of solvent introduced into the compartment of the shell must be sufficient for all the roughnesses in the portion of road delimited by the shell to be covered by the solution.

All other things being equal, good results are generally obtained when the thickness of the layer of solution in the compartment delimited by the shell is equal to at least 1 mm or preferably greater than 2 mm.

The maximum amount of solvent which is not to be exceeded in the compartment of the shell is conditioned by the need to prevent solution from leaking out underneath the gasket of the shell, under the action of the hydrostatic pressure of the solution in the compartment of the shell. All other things being equal, this maximum value depends on a large number of factors which include, in particular, the roughness of the road, the nature of the gasket of the shell, the cross-section and the shape of the shell and the nature, in particular the viscosity, of the solvent used.

By way of example, amounts of solvent which are suitable in the case of a rough hydrocarbon road surfacing are those which make it possible to achieve, in the compartment delimited by the shell on the road, a layer of solution having a thickness of between 2 and 50 mm, excellent results generally being obtained with layer thicknesses of between 5 and 20 mm.

In carrying out the process according to the invention, the electrical parameter measured must be chosen from amongst those which are representative of the concentration of chemical deicer in the layer of solution. Examples of suitable electrical parameters are the dielectric constant of the solution, its electrical resistivity, its electrical conductivity, its magnetic permeability, its characteristics relating to the propagation of electromagnetic waves, such as its absorption, refraction and diffraction characteristics, and an electrical measurement of its pH. Particularly preferred electrical parameters are the electrical resistivity and conductivity.

According to the invention, the electrical parameter of the layer of solution can be measured in situ in the compartment of the shell, whilst the latter is positioned on the road. For this purpose, according to a first embodiment of the process according to the invention, two electrodes, spaced apart from one another by a predetermined distance, are immersed in the layer of solution contained in the compartment of the shell, and the electrical resistance of the layer of solution separating the electrodes is measured. The electrical resistivity of the layer of solution contained in the shell is deduced therefrom by means of the relationship:

$$\rho = R \times \frac{S}{l}$$

in which $\rho$ denotes the resistivity of the solution, R denotes the electrical resistance measured, S denotes the surface area of the electrodes and $l$ denotes the distance separating the two electrodes.

As a variant, it is also possible, according to the invention, to remove a fraction or the whole of the layer of solution contained in the compartment of the shell, and then to measure the electrical parameter of the solution outside the shell. For this purpose, according to a second embodiment of the process according to the invention, it is possible, for example, to cause the fraction of solution removed from the shell to circulate in contact with two electrodes, and measure the electrical resistance of the solution between the two electrodes. In this manner, the resistivity of the solution is deduced by means of the abovementioned relationship.

In the process according to the invention, the solution present in the compartment of the shell is preferably subjected to mechanical stirring during the introduction of the solvent into the said compartment, in order to accelerate the homogenisation of the solution. For this purpose, it is possible, for example, to employ stirrers, such as brushes, which are moved inside the shell.

According to a preferred embodiment of the process according to the invention, in order to agitate the solution, the solvent is sprayed under pressure against the road during its introduction into the shell.

In the process according to the invention, the measurement of the electrical parameter of the layer of solution of chemical deicer, contained in the compartment of the shell, is a measure of the proportion of chemical deicer in this solution; consequently, since the amount of solvent introduced into the shell and the area delimited by the latter on the road are known, it is a measure of the amount of chemical deicer per unit area of the road.

In order to carry out the process according to the invention, it is possible to use a device which, according to the invention, comprises a shell designed to be applied in a leaktight manner to the road, a member for introducing, into the shell, a defined volume of a solvent for the chemical deicer, and a cell for measuring an electrical parameter of liquids.

In the device according to the invention, the purpose of the member for introducing solvent into the shell is to deliver a defined predetermined volume of solvent into the compartment of the shell. According to the invention, it can advantageously consist of a syringe. The latter is preferably equipped with a sprayer directed towards the bottom of the shell, so as to ensure the projection and dispersion of the solvent onto the road. The useful volume of the syringe must be chosen as a function of the cross-section of the shell, so that, when the latter is positioned on a road, the syringe is capable of introducing therein a volume of solvent which is compatible with the formation of a layer of solution of the required thickness, as defined above, for example a layer of solution having a thickness equal to at least 2 mm and preferably of between 5 and 50 mm. The useful volume of the syringe must therefore be equal to the volume delimited between the wall of the shell, its bottom and a plane which is parallel to the bottom and removed from the latter by a distance equal to the required thickness of the layer of solution in the shell.

As a variant, the syringe can be replaced by a pneumatic injector or any other known apparatus which is capable of spraying and projecting the solvent under pressure into the shell.

The measuring cell is designed to measure an electrical parameter of the solution formed in the shell, after the solvent and, if necessary, a suitable reagent have been introduced. A series of examples of electrical parameters which can be used within the scope of the invention have been mentioned above.

In a first embodiment of the device according to the invention, the measuring cell comprises at least two electrodes which are located in the shell and are connected to an apparatus, which is in itself known, for measuring electrical resistance or conductance, such as an ohmmeter or a bridge for measuring resistance or conductance, for example a Wheatstone bridge. The electrodes, for example two in number, can be located diametrically opposite one another near the wall of the shell. As a variant, the electrodes can also consist of one electrode located along the axis of the shell and a series of electrodes which are located at the periphery of the shell and are connected to one another.

In this embodiment of the device according to the invention, the dimensions of the electrodes and their position in the shell must be fixed so that the electrodes are immersed in the layer of solution formed in the shell, after the solvent has been introduced into the shell.

In a second embodiment of the device according to the invention, the measuring cell consists of a tubular chamber which is connected to a member for transferring a solution of the chemical deicer from the shell into the tubular chamber, the said tubular chamber containing two electrodes connected to an apparatus for measuring resistance or conductance.

In this particular embodiment of the invention, the measuring cell generally consists, in a manner which is in itself known, of an enclosure containing two electrodes of defined surface area, which are spaced apart from one another by a predetermined distance, the apparatus for measuring resistance or conductance being, for example, an ohmmeter or a measuring bridge such as a Wheatstone bridge.

The essential purpose of the member for transferring the solution of chemical deicer into the measuring cell is to send, into the measuring cell, at least a fraction of the solution of chemical deicer formed in the compartment delimited by the shell, after the latter has been positioned on a road treated with a chemical deicer and after it has been provided with a defined volume of solvent using the abovementioned member for introducing solvent. The transfer member can consist, for example, of a manually or electrically operated lift and force pump which is capable of removing, by suction, the abovementioned fraction of solution from the shell and then delivering it into the measuring cell.

Since the device according to the invention is designed so that the same amount of solvent is introduced into the shell for each determination, it can easily be calibrated using solutions having known concentrations of chemical deicer and can directly show values of the amount of deicer per unit area of the road, in response to the measurements of the electrical parameter.

In order to take account of the influence of the ambient temperature on the value of the electrical parameter of the solution, it is possible, according to an advantageous embodiment of the invention, to provide the measuring cell with a member for correcting the influence of the temperature. This member can, for example, consist of a calibrated variable resistance which can be operated manually or automatically by means of an electronic circuit.

The process and the device according to the invention exhibit the advantage that they make it possible to determine rapidly, precisely and easily the amount of chemical deicer present on a road. Consequently, the invention makes it possible, at any time, to check whether an additional spreading of chemical deicer proves necessary and, if so, to calculate the amount of deicer which should be spread per unit area of the road.

The invention will be explained by means of the following application examples, with reference to the attached drawings.

Figure 1:
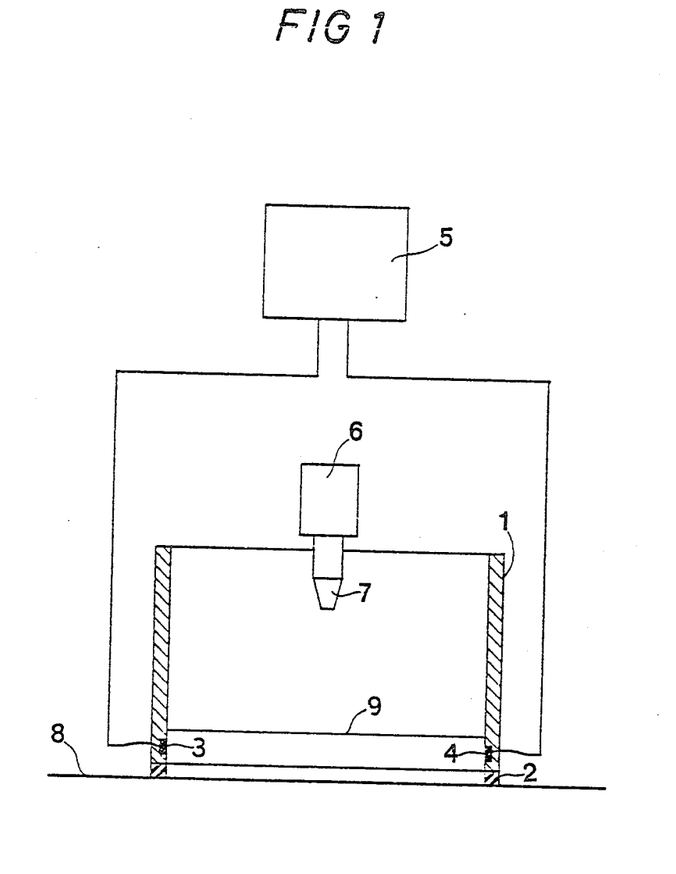
FIG. 1 is a schematic representation, partially in vertical transverse section, of a particular embodiment of the device according to the invention.

According to the invention, the device shown in FIG. 1 comprises a rigid cylindrical shell 1, made, for example, of a synthetic material such as polyvinylidene fluoride, polyethylene, polyvinyl chloride or a polyester. The shell 1 is equipped, on one edge, with an elastic gasket 2 which is designed to ensure efficient watertightness when it is positioned with the shell on a road surfacing. The gasket 2 can, for example, consist of a rubber ring glued to the periphery of the shell, or of an annular rubber strip possessing a U-shaped transverse section, in which strip the lower edge of the shell is inserted and sealed, for example by glueing. As a variant, it is also possible to use, for the gasket 2, an annular hose which is elastically deformable and inflated with air or another gas. In order to improve the leaktightness of the gasket 2, it can advantageously be covered with a film of a hydrophobic material, for example with silicone.

The device of FIG. 1 also comprises a cell which is designed to measure the electrical resistivity of a solution of chemical deicer, contained in the shell. For this purpose, the shell 1 is equipped, on its inner face, near the gasket 2, with two diametrically opposite electrodes 3 and 4, which are connected to a member 5 for measuring resistance, which can, for example, be a measuring bridge. The two electrodes 3 and 4 are, for example, made of nickel, silver, stainless steel or brass.

The device of FIG. 1 is also equipped with a member 6 for introducing a defined volume of water, under pressure, into the shell 1. This member 6 consists, for example, of a manually operated syringe. Its outlet orifice is directed along the axis of the shell 1; it is advantageously equipped with a sprayer 7.

In order to carry out the process according to the invention using the device of FIG. 1, the shell 1 is positioned on the surface of the road 8 on which a chemical deicer, consisting, for example, of particles of sodium chloride or calcium chloride or of a film of brine, has been spread. The gasket 2 ensures the leaktightness between the shell 1 and the surface of the road 8. A defined volume of water is then introduced into the shell using the syringe 6. During its introduction into the shell, the water is sprayed by the sprayer 7 and projected onto the road, and this accelerates the dissolution of the chemical deicer and ensures the production of a homogeneous solution of the deicer in the shell. The amount of water introduced into the shell 1 by the syringe 6 is fixed so that the layer of solution 9, thus formed in the shell, completely bathes the two electrodes 3 and 4.

After the required amount of water has been introduced into the shell 1, the electrical resistance of the layer of solution 9 between the electrodes 3 and 4 is measured using the measuring bridge 5. The value of the resistance recorded is a measure of the concentration of the solution of chemical deicer, and, consequently, since the area of the internal transverse section of the shell is known, it is a measure of the amount of deicer present, per unit area, on the road 8.

EXAMPLE 1

Calcium chloride was uniformly spread on a concrete road at the rate of 0.8 g of calcium chloride per $m^2$ of road, and the process according to the invention was applied, using, for this purpose, the device shown in FIG. 1.

The shell 1 of the device had an internal diameter of 9 cm and the useful volume of the syringe 6 was equal to 40 $cm^3$.

The resistance of the layer of solution 9 between the electrodes 3 and 4 was equal to 3.57 $k\Omega$.

EXAMPLES 2 to 6

The experiment of Example 1 was repeated with amounts of calcium chloride on the road which were respectively equal to the following values: 2 $g/m^2$, 2.2 $g/m^2$, 2.8 $g/m^2$, 4.1 $g/m^2$ and 5.9 $g/m^2$.

The results of Examples 1 to 6 have been recorded in the following table:

| Example (No.) | Amount of $CaCl_2$ on the road ($g/m^2$) | Resistance of the layer of solution ($k\Omega$) |
|---|---|---|
| 1 | 0.8 | 3.57 |
| 2 | 2.0 | 2.70 |
| 3 | 2.2 | 2.50 |
| 4 | 2.8 | 2.04 |
| 5 | 4.1 | 1.56 |

| Example (No.) | Amount of CaCl$_2$ on the road (g/m$^2$) | Resistance of the layer of solution (kΩ) |
|---|---|---|
| 6 | 5.9 | 1.18 |

Figure 2:
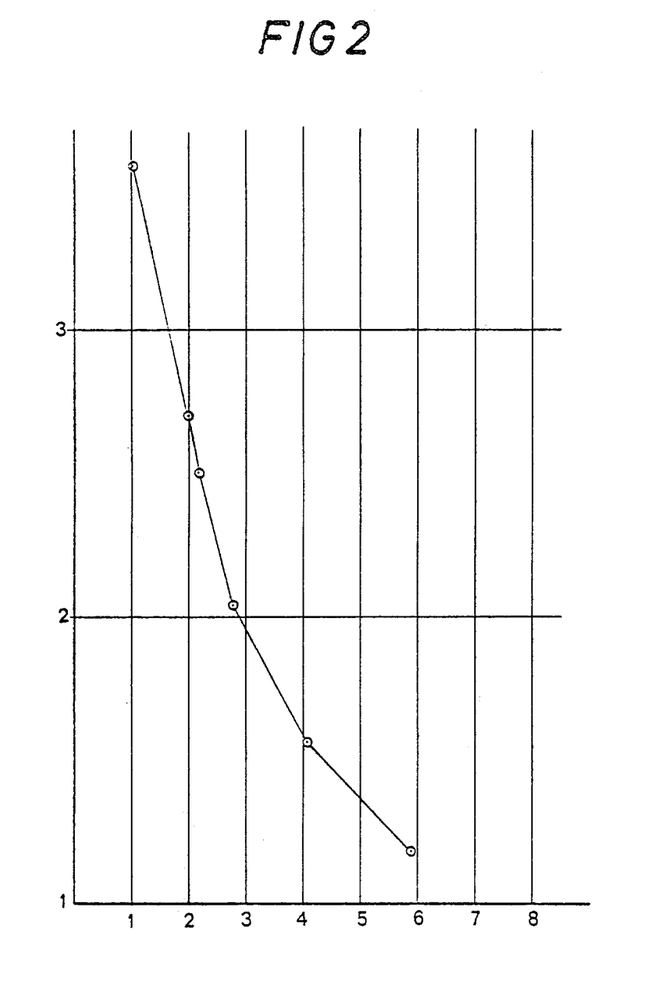
FIG. 2 is a calibration graph for the device of FIG. 1.

Furthermore, these results are reproduced on the graph of FIG. 2, in which the abscissa scale shows the amount of calcium chloride on the road, expressed in g/m$^2$, and the ordinate scale shows the measured value of the resistance of the layer of solution in the shell, expressed in kΩ.

Observation of the graph shows that, after calibration with a few known values of the amount of calcium chloride, the device and the process according to the invention are capable of providing a precise measurement of the amount of calcium chloride present per unit surface area of the road. In fact, it suffices, in each particular case, to plot the measured value of the electrical resistance on the calibration curve of FIG. 2 in order to determine, on the abscissa scale, the corresponding value of the amount of calcium chloride per m$^2$ of the road.

Calibration curves similar to those of the graph of FIG. 2 can obviously be set up for each chemical deicer envisaged, such as, for example, sodium chloride, calcium chloride, defined mixtures of magnesium chloride and sodium chloride, brines and the like.

Figure 3:
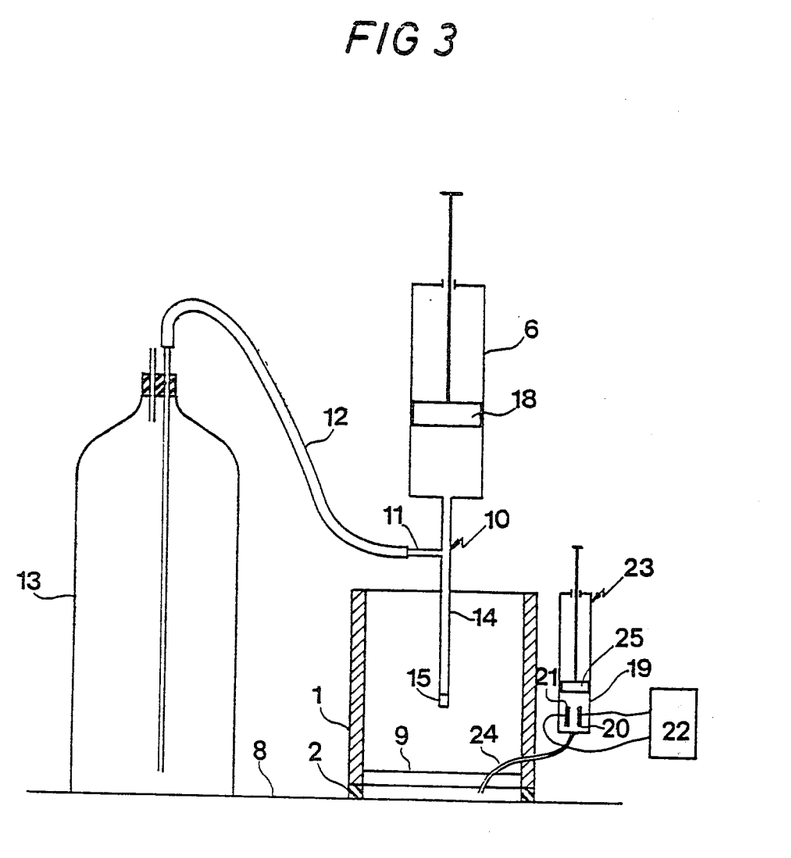
FIG. 3 is a schematic representation, partially in vertical transverse section, of another embodiment of the device according to the invention.
Figure 4:
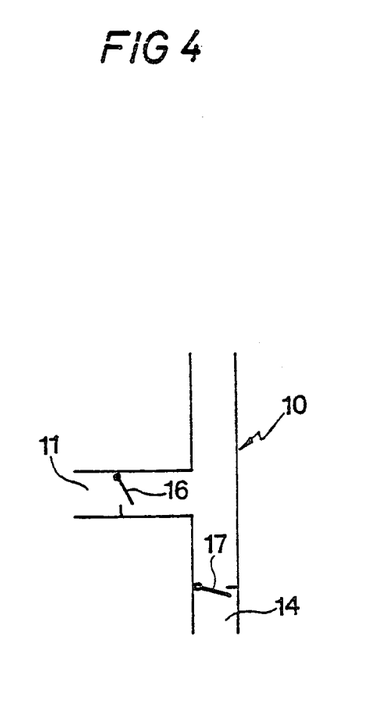
FIG. 4 shows, schematically and on a larger scale, a detail of the device of FIG. 3.

In the embodiment shown in FIG. 3, the member 6 for introducing a defined volume of water, under pressure, into the shell 1 comprises a manually operated syringe, the outlet orifice of which is connected to a three-way dispenser 10, shown on a larger scale in FIG. 4. The channel 11 of the dispenser 10 is connected, via a flexible tube 12, to a flask 13 which is intended to contain water, whilst the channel 14 is extended inside the shell 1 and terminated by a sprayer 15 directed towards the bottom of the shell 1.

The channels 11 and 14 of the dispenser 10 are each provided with a valve, 16 and 17 respectively. The latter are normally kept in the closed position by means of return springs which are not shown; they are designed in such a way that, under the action of an ascending movement of the piston 18 in the chamber of the syringe 6, the channel 11 is open and the channel 14 is blocked, while, under the action of a descending movement of the piston 18, the channel 11 is blocked and the channel 14 is open.

A spring, which is not shown, can advantageously be provided in order to bring the piston 18 automatically into its extreme upper position.

In the device of FIG. 3, the cell 19 for measuring resistivity is housed outside the shell 1, and a member 23 is provided for transferring a liquid solution from the shell 1 into the cell 19.

The cell 19 consists of a tubular enclosure containing two electrodes 20 and 21 of well-defined surface area, which are spaced apart from one another by a predetermined distance, for example 2 mm, and are connected to an apparatus 22 for measuring electrical resistance; this apparatus can advantageously consist of a measuring bridge, for example a Wheatstone bridge.

The transfer member 23 consists of a syringe located in the extension of the tubular enclosure of the measuring cell 19; a flexible tube 24, fixed to the lower end of the enclosure of the cell 19, passes through the wall of the shell 1 and emerges near the bottom of the latter.

In order to carry out the process according to the invention using the device of FIG. 3, the flask 13 is first filled with water, and then the shell 1 is positioned on the surface of the road 8 on which a chemical deicer, consisting, for example, of particles of sodium chloride or calcium chloride or of a film of brine, has been spread. The elastic gasket 2 ensures the leaktightness between the shell 1 and the surface of the road 8.

The piston 18 of the syringe 6 is then operated in order to bring it from its extreme lower position to its extreme upper position and thus to fill the syringe wih a defined volume of water drawn off from the flask 13 via the tube 12. The piston 18 is then pushed back as far as its extreme lower position, the result of which is to spray the water from the syringe, through the sprayer 15, onto the portion of the road 8 circumscribed by the shell 1. A layer 9 of an aqueous solution of the chemical deicer is thus formed on this portion of the road.

The piston 25 of the syringe 23 is then operated in order to suck a fraction or the whole of the layer of solution 9 through the measuring cell 19, and the electrical resistance of the layer of solution between the electrodes 20 and 21 is measured using the measuring bridge 22. The value of the resistance recorded is a measure of the resistivity of the solution of chemical deicer and, consequently, of the concentration of chemical deicer therein. Since the area of the transverse section of the shell is known, this value is a measure of the amount of chemical deicer present, per unit area, on the road 8.

Figure 5:
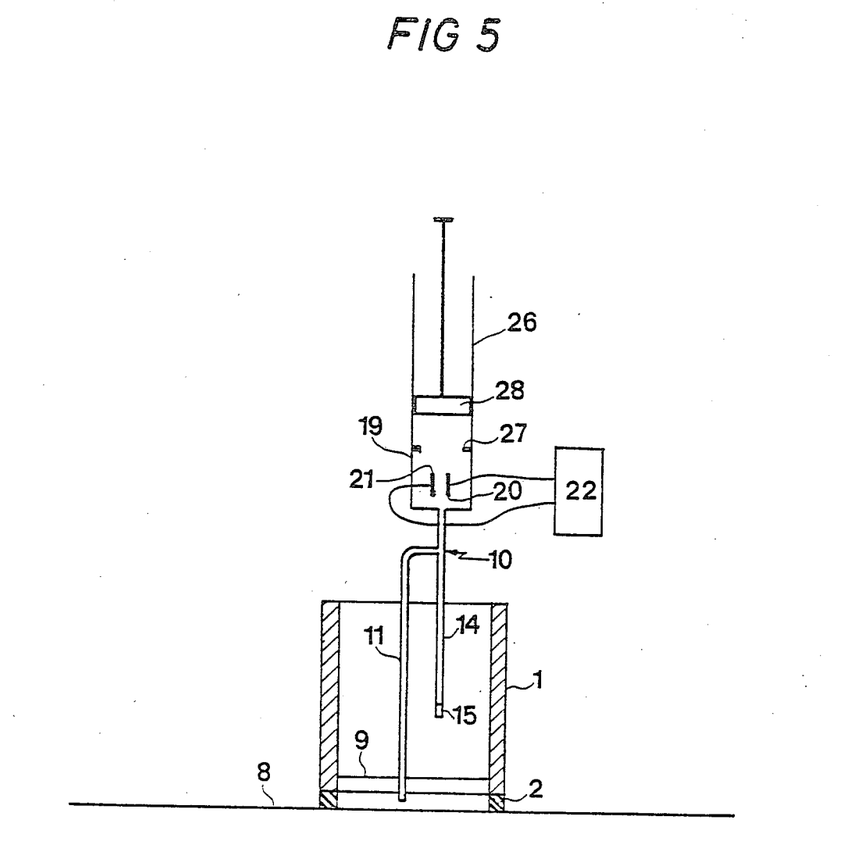
FIG. 5 is a schematic representation, partially in vertical transverse section, of a third embodiment of the device according to the invention.

FIG. 5 shows a modified embodiment of the device of FIG. 3. In this modified embodiment, a single syringe 26, located in the extension of the measuring cell 19, constitutes both the member for introducing water into the shell 1 and the member for transferring the solution of deicer from the shell into the measuring cell 19. The latter is connected, at its lower end, to a three-way dispenser 10 of the type represented schematically in FIG. 4 and described above. The channel 14 of the dispenser 10 is used for the admission of the water from the syringe 26 into the shell 1 and it is terminated, for this purpose, by a sprayer 15. The channel 11 of the dispenser 10 is extended as far as the region of the bottom of the shell 1; it is used to transfer the solution of chemical deicer from the shell 1 into the measuring cell 19.

In order to carry out the process according to the invention using the device of FIG. 5, the piston 28 is extracted from the syringe 26 an the chamber of the syringe is filled with a defined volume of water. Since the valves 16 and 17 are kept in the closed position by means of their respective return springs, they prevent the water from flowing out of the syringe 26.

The piston 28 is then moved downwards in the syringe 26 as far as the stops 27, the result of which is to drive all the water from the syringe 26 into the shell 1, via the channel 14 of the dispenser 10. The piston 28 is then raised in order to suck the layer of solution 9 (or a fraction of the latter) into the cell 19 and the syringe 26, via the channel 11 of the dispenser 10.

What is claimed is:

1. Process for determining a chemical deicer on a road, comprising: positioning a shell of predetermined cross section on the road; introducing into the compartment delimited by the shell and the road, a fixed amount of solvent for said chemical deicer to form a layer of solution; and measuring an electrical parameter of the resulting layer of solution.

2. Process according to claim 1, characterised in that the amount of solvent introduced into the compartment of the shell is fixed so that the layer of solution achieves a thickness equal to at least 2 mm in this compartment.

3. Process according to claim 1 or 2, wherein the electrical parameter of the solution is measured in situ in the compartment of the shell.

4. Process according to claim 3, wherein, in order to measure the electrical parameter of the layer of solution contained in the compartment of the shell, at least two electrodes are immersed in this layer of solution and the resistance of the said layer of solution between the electrodes is measured.

5. Process according to claim 1 or 2, wherein, in order to measure the electrical parameter of the layer of solution contained in the compartment of the shell, at least a fraction of the layer of solution is removed from the compartment of the shell, said fraction of solution is caused to circulate in contact with two electrodes and the electrical resistance of the solution between the two electrodes is measured.

6. Process according to claim 1 or 2, wherein said solvent is introduced into the compartment of the shell by spraying said solvent against the road.

7. Device for determining a chemical deicer on a road, comprising a shell designed to be applied in a leaktight manner to the road, a member for introducing, into the shell, a defined volume of a solvent for the chemical deicer, and a cell for measuring an electrical parameter of liquids.

8. Device according to claim 7, wherein said measuring cell comprises at least two electrodes which are located in the shell and are connected to an apparatus for measuring electrical resistance or conductance.

9. Device according to claim 7, wherein said measuring cell comprises a tubular chamber connected to a member for transferring a solution of the chemical deicer from the shell into the tubular chamber, said tubular chamber containing two electrodes connected to an apparatus for measuring electrical resistance or conductance.

10. Device according to claim 7, 8 or 9, wherein said member for introducing the solvent into the shell comprises a syringe equipped with a sprayer which is directed towards the bottom of the shell.

* * * * *